United States Patent [19]
Cottone

[11] Patent Number: 5,776,140
[45] Date of Patent: Jul. 7, 1998

[54] STENT DELIVERY SYSTEM

[75] Inventor: Robert Cottone, Ft. Lauderdale, Fla.

[73] Assignee: Cordis Corporation, Miami Lakes, Fla.

[21] Appl. No.: 683,063

[22] Filed: Jul. 16, 1996

[51] Int. Cl.⁶ ................................... A61B 17/00
[52] U.S. Cl. ................ 606/108; 606/191; 606/198
[58] Field of Search .................... 606/108, 192, 606/194, 195, 198; 623/1, 12

[56] References Cited

U.S. PATENT DOCUMENTS

| 5,391,172 | 2/1995 | Williams et al. | 606/108 |
| 5,415,664 | 5/1995 | Pinchuk | 606/108 |
| 5,453,090 | 9/1995 | Martinez et al. | 604/53 |
| 5,458,605 | 10/1995 | Klemm | 606/108 |
| 5,591,172 | 1/1997 | Bachmann et al. | 606/108 |

Primary Examiner—Gary Jackson
Assistant Examiner—David O. Reip
Attorney, Agent, or Firm—Gerstman, Ellis & McMillin, Ltd.

[57] ABSTRACT

An implantable medical device such as a stent may be implanted within a patient by the steps of advancing a catheter having a balloon into the patient, in which the catheter carries the medical device in a position surrounding the catheter balloon. The catheter also carries an outer, semi-flexible sheath surrounding at least part of the catheter and the medical device. The medical device and flexible sheath are advanced together into a patient with the catheter, to position the device at a desired location while the device is enclosed in the sheath. Then, the sheath is retracted to expose the medical device to the exterior. The balloon is inflated to radially expand the device. Then the catheter and sheath are withdrawn from the patient. The catheter described can be used to implant a stent without the need for a guiding catheter. Also, x-ray contrast media can be applied to the vicinity of the medical device without removal of the guidewire.

29 Claims, 2 Drawing Sheets

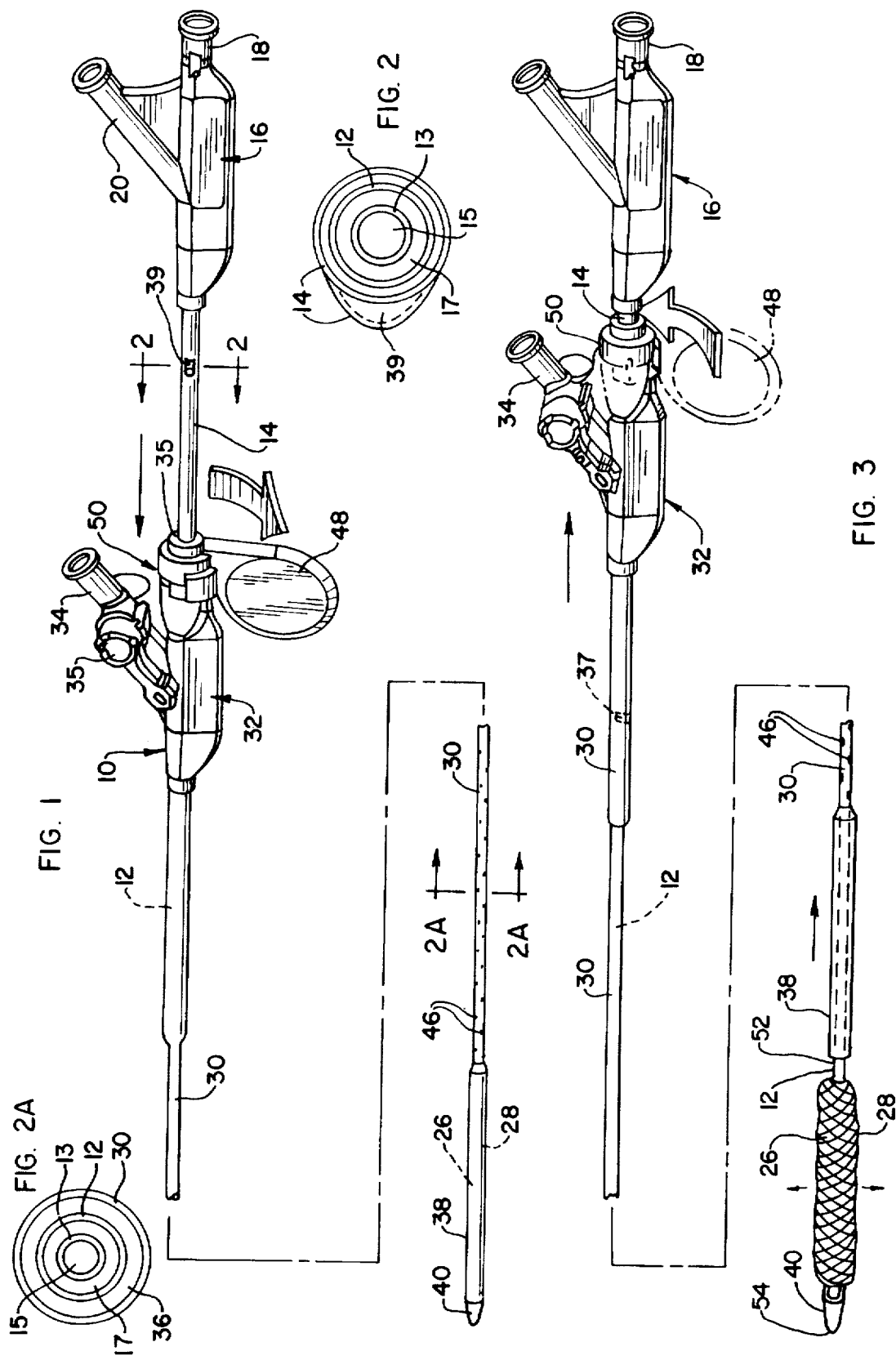

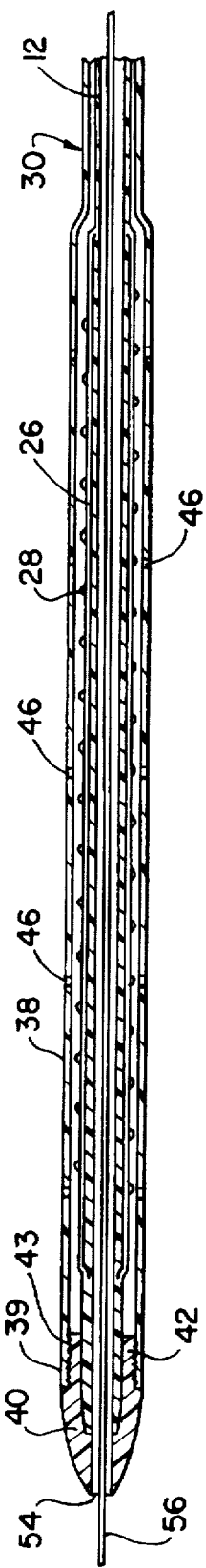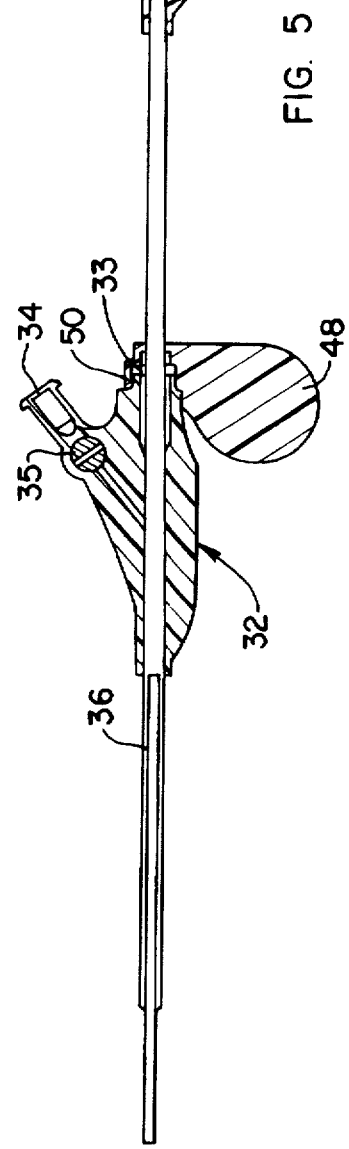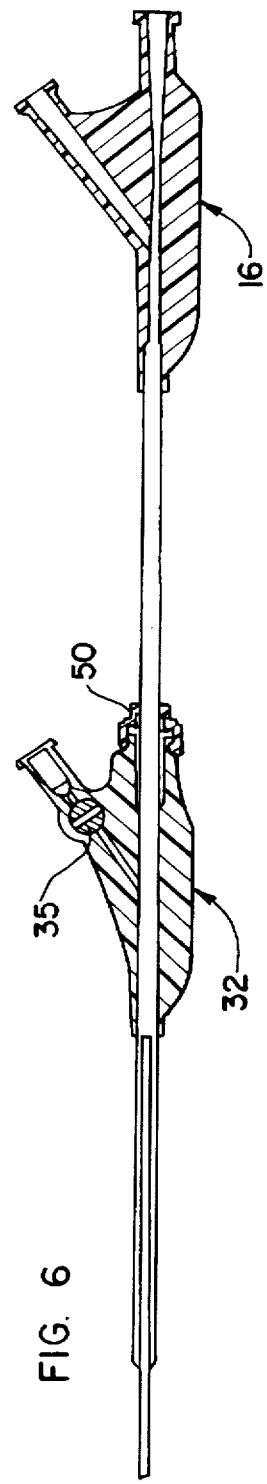

STENT DELIVERY SYSTEM

BACKGROUND OF THE INVENTION

Stents are well-known for use in various medical procedures including procedures for widening blood vessels on a permanent basis. Basically, a stent is a typically tubular structure which is passed into a patient, typically on a catheter, in a collapsed, minimum-diameter form. When the stent has been properly placed in a blood vessel, for example, or any other body duct or organ, a catheter balloon within the stent is expanded, forcing the stent into a typically permanently expanded configuration, where it serves rather as a scaffold to support the interior of a blood vessel or the like in a permanently expanded configuration.

Many different types of stents are known. Typically, a stent is inserted into a blood vessel through the interior of a guiding catheter which must be preplaced in the patient, to guide the stent and the catheter which carries it to a desired location, where the stent will be expanded by the balloon of the catheter that carries it. Typically, the guiding catheter is emplaced by following a preplaced guidewire to the desired position. Thus, to emplace a stent, it is generally necessary to have at least a catheter introducer sheath, a guidewire, a guiding catheter, a balloon-carrying stent catheter, and the stent itself.

By this invention, a stent may be implanted without the need for a pre-emplaced guiding catheter while body tissues through which the stent is advanced are still protected from scraping by the irregularities that are typically found in a stent. This is accomplished with little increase in the diameter of the overall system, which means that the system may be used to place a stent deeply into small-sized peripheral arteries or other small body lumens. Also, the stent remains protected against bending by calcified lesions or the like across which it must pass, prior to expansion.

Improved radiographic assessment of the positioning of the stent can be provided in accordance with this invention. Also, the stent is reliably held in position on the catheter balloon which it surrounds as the stent application system of this invention is advanced into a patient.

DESCRIPTION OF THE INVENTION

By this invention, an implantable medical device such as a stent may be deployed in a patient by the steps which comprise: advancing a balloon catheter, a stent, and a catheter sheath together into the patient, where the catheter carries the stent in a position surrounding a catheter balloon, and the catheter also carries an outer, semi-flexible sheath surrounding at least part of the catheter and the stent.

The catheter, stent, and semi-flexible sheath are advanced together into the patient to position the stent at a desired location while the stent is enclosed in the sheath and surrounding the balloon.

One then retracts the sheath to expose the stent. One can then inflate the balloon to radially expand the stent. Then, the catheter and sheath may be withdrawn from the patient.

By this invention, it is also preferred to, before and/or after the inflation of the balloon and radial expansion of the stent, to pass x-ray contrast fluid to the vicinity of the stent between the catheter and the sheath, to x-ray visualize the position of the stent. Improvements in x-ray visualization are achieved because a larger flow of x-ray contrast fluid can pass in the tubular path between the catheter and the sheath, when compared with the flow of x-ray contrast fluid in the manner of the prior art, where the x-ray contrast fluid passes through the guidewire lumen of a prior art stent catheter after removal of the guidewire. Thus, by this invention, the guidewire used herein does not have to be removed, and increased fluid flow can be provided because of the increased cross-sectional area of flow between the exterior of the catheter and the sheath, when compared with the cross sectional flow area of a lumen within the catheter. Even before retraction of the sheath it can be possible to provide a good flow of x-ray contrast medium to a vessel in which the stent resides, to obtain good x-ray visualization.

As a further advantage of this invention, the catheter, stent, and sheath may be advanced into the patient without the use of a guiding catheter. The outer sheath, which travels with the catheter and stent, may serve the function of the guiding catheter, while also serving the function of a radiographic catheter, providing abundant quantities of x-ray contrast medium to the position of the stent. Also, walls of blood vessels or other body lumens may be protected by the sheath from injury by the advancing stent, while the stent also may be protected from bending or damage if it is forced past a calcified area.

Preferably, the sheath used in this invention defines side holes positioned adjacent to the stent, typically in a distal end portion of the sheath, to facilitate the flow of x-ray contrast fluid out of the sheath. X-ray contrast fluid may thus be applied to the desired stent area whether the sheath has been retracted from the stent or not.

Preferably, the sheath has a wall thickness of no more than about 0.015 inch, so that the increase in maximum diameter of the stent catheter system of this invention can be very small, when compared with corresponding prior art catheters where the stent is open and exposed to the exterior. Also, it is preferred for the sheath used in this invention to be of sufficient stiffness to avoid wrinkling and axial collapsing as the sheath is advanced with the catheter and stent into the patient. To accomplish this, the sheath may be made of a material which would be quite stiff in the customary form of a thicker tube but retains adequate flexibility at such a small wall thickness, for example, polyimide plastic.

Preferably, the catheter and sheath define proximal ends, and are connected together at those ends, each through a separate hub. One of the hubs, preferably the hub connecting the sheath, may be slidably movable along the catheter, permitting movement of the sheath between an advanced position which surrounds the stent and a retracted position where the sheath is longitudinally spaced from the stent. Specifically, the catheter may define a proximal portion of non-circular cross section, for example a teardrop-shaped cross section. The hub which is connected to the sheath is slidable on this proximal portion between the advanced and retracted positions described above in a manner which prevents rotation about the longitudinal axis of the catheter. This can be accomplished by providing to the sheath hub a passageway through which the catheter proximal portion slides, which passageway may also be of substantially non-circular cross section, and typically the same non-circular cross section, thus preventing rotation of the sheath hub about the catheter longitudinal axis. This non-rotational sliding relationship between the two hubs and the other parts of the system prevents twisting of the stent as it is advanced and manipulated within the patient.

It is also preferred for the hub connected to the sheath to have a lock to secure the sheath hub in the advanced position so that the sheath remains in its position surrounding the stent, until it is specifically desired to retract the sheath. In that circumstance, the lock is released to permit the sheath to be retracted.

It is also preferred for the sheath to define a distal tip. The sheath distal end is releasably retained by the catheter distal tip until the sheath is retracted. This may be accomplished by forming the catheter distal tip to have at least portions which have an outer diameter slightly larger than the outer diameter of the sheath at the distal end thereof. The distal tip may also define some rings or the like which are typically perpendicular to the catheter longitudinal axis, so that the sheath may advance into a circumferential pressure seal relation about the rings. Typically, the catheter distal tip is made of an elastomeric material, so that a good pressure seal can be achieved with the sheath. Thus the sheath can be advanced without engaging in an undesirable "fish mouth" configuration, in which a portion of the sheath extends outwardly, forming an opening to its bore or lumen. This, in turn, can cause coring of tissue from the body lumen in which the catheter is advancing, which of course is very undesirable, and can be substantially eliminated by the use of a distal tip as described above.

DESCRIPTION OF DRAWINGS

FIG. 1 is a perspective view of the stent deploying catheter of this invention, in its position in which the catheter and stent are to be advanced into a patient;

FIG. 2 is a sectional view taken along line 2—2 of FIG. 1;

FIG. 2A is a sectional view taken along line 2A—2A of FIG. 1;

FIG. 3 is a perspective view of the stent deploying catheter in its position in which the stent is being expanded by expansion of the catheter balloon;

FIG. 4 is an enlarged, longitudinal sectional view of the distal tip of the stent deploying catheter of FIG. 1, with the stent attached;

FIG. 5 is a longitudinal sectional view of the two hubs of the stent deploying catheter of the previous drawings, with the hub for the sheath being in locked, advanced configuration; and FIG. 6 is a longitudinal sectional view similar to FIG. 5, but with the hub of the sheath shown in unlocked configuration to permit sliding of the sheath.

DESCRIPTION OF SPECIFIC EMBODIMENT

Referring to the drawings, a catheter 10 is provided comprising a tubular catheter body 12 (FIG. 3) which is conventionally connected to a first hub 16. A proximal, tubular, stainless steel section or "hypotube" 14 surrounds a proximal portion of catheter body 12, and is also connected to hub 16. Tubular catheter body 12 is enclosed in FIG. 1, but visible in FIGS. 2, 2A and 3. Inner, catheter tube 13 is also conventionally provided to define a guidewire lumen 15 and a balloon inflation lumen 17 within tubular body 12.

Catheter body 12 and proximal catheter section 14 are thus of the multiple lumen type, which lumens 15, 17 respectively communicate with a pair of ports 18, 20 in hub 16. Lumen 15 connects with port 18 and comprises a guidewire lumen. Lumen 17 connects with port 20, and also communicates with a catheter balloon 26 carried on catheter body 12 (FIG. 3) in conventional manner. A stent 28, which may be of a conventional crossing wire or apertured tube design, is carried over and around balloon 26 in conventional manner.

Catheter 10 also carries an outer, semi-flexible sheath 30, surrounding most of catheter body 12 and connected to a second hub 32. Second hub 32 defines a side port 34, which communicates with the tubular space 36 (FIG. 2A) between catheter body 12 and sheath 30.

Second hub 32 is slidable along hypotube 14 between the two positions of FIG. 1 and FIG. 3, taking sheath 30 along with it as it slides. In the forward sliding position of FIG. 1, distal end portion 38 of sheath 30 occupies a position overlying balloon 26 and stent 28, so that the stent is enclosed and out of contact with the exterior. The distal end 52 of sheath 30 can engage and, if desired enter into, sealing relation with a catheter distal tip 40, which is carried at the distal end of catheter body 12. As shown in FIG. 4, some of distal end 38 of sheath 30 can overlie a proximal portion 42 of tip 40, which proximal portion carries sealing rings 43 to provide a seal between the sheath 30 and the tip until the sheath is withdrawn.

Distal portion 38 of sheath 30 may be somewhat radially enlarged as shown relative to other portions of sheath 30, to provide room to receive stent 28 in its collapsed configuration. A portion of sheath 30 proximal to end portion 38 may also define a series of side holes 46, for flow of x-ray contrast solution outwardly from the interior of the catheter of the catheter to areas of tissue surrounding stent 28.

Second hub 32 defines an annular seal 33 to prevent fluid leakage from annular space 36, and a lock 50 for selectively preventing and permitting the sliding motion of hub 32 and sheath 30 along the rest of the catheter, to provide or to prevent the desired movement between the positions of FIGS. 1 and 3. A hub lock 50 comprises a rotary handle 48, which is shown in the locked position in FIG. 1, with the handle being rotated 90 degrees in FIG. 3 so that it is no longer visible, and occupies the unlocked position. As handle 48 occupies the position of FIG. 1, rotatable lock 50 engages in a locking relation with a recess 37 (FIG. 3) carried on the exterior of hypotube 14, to prevent proximal motion of second hub 32 and sheath 30. However, when handle 48 is rotated to the position of FIG. 3, rotatable lock 50, attached to handle 48, moves out of engagement with recess 37 of hypotube 14, thus permitting second hub and sheath 30 to be proximally withdrawn toward first hub 16. With this motion, distal end portion 38 of sheath 30 is correspondingly withdrawn, exposing balloon 26 and stent 28 as shown in FIG. 3. A similar locking recess 39 is shown for locking hub 32 in the position of FIG. 3.

Then, balloon 26 may be inflated through lumen 17, correspondingly causing the expansion of stent 28, to provide its permanent emplacement in a blood vessel or the like. Following this, balloon 26 may be deflated again, by control of fluids through lumen 17, so that the catheter may be withdrawn from the patient, leaving stent 28 in its desired position.

At any time during these proceedings it can be seen that x-ray contrast fluid can be applied to the area of and surrounding stent 28. For example, in the configuration of FIG. 1, x-ray contrast fluid may flow through port 34 of second hub 32 into the annular space 36 between catheter body 12 and sheath 30. This space serves as a flow channel for the x-ray contrast fluid, to flow distally for about the entire length of the catheter until it encounters the holes 46 near the distal sheath end portion 38. The x-ray contrast fluid can flow out of the catheter at that point in an abundant flow, provided by the relatively large flow cross section of tubular space 36, to provide a clear indication to the surgeon as to the location of stent 28.

Then, after emplacement of the stent as in FIG. 3, it still is possible for x-ray contrast fluid to flow through tubular space 36 and out of the side portions 46 and the distal end 52 of sheath 30, to provide good x-ray visibility of the location of stent 28, particularly if distal end portion 38 of the sheath is upstream in terms of blood flow from the stent. It should also be noted that the application of x-ray contrast medium can be applied without removal of a guidewire 56 (FIG. 4), which may extend through the catheter from guidewire port 18 along its entire length, and out of distal aperture 54 of distal tip 40. Accordingly, the guidewire may remain in its position through the entire operation and use of this catheter, including a step or steps of the use of contrast medium to provide x-ray visualization of the position of stent 28.

Following the implantation of stent 28, the catheter and sheath are easily withdrawn, while the guidewire 56 may remain in position if desired.

Port 34 may have its flow controlled by a stopcock 35, for selective application of x-ray contrast medium.

Sheath 30 may comprise a tube having a wall thickness of no more than about 0.015 inch, to be of sufficient stiffness to avoid wrinkling and axial collapsing as the sheath is advanced with the catheter and stent into the patient. Thus, it is generally preferred for the sheath to be made of a strong, semi-flexible plastic, for example, polyimide plastic or other material having similar properties of good stiffness plus a desired measure of flexibility.

Hypotube 14 can be seen in FIG. 2 to have an outer periphery of non-circular cross section, specifically of generally teardrop configuration, although other shapes may also be used, for example rectangular or the like. Hub 32 may define a central aperture or bore 35 that slides along and surrounds 14 as hub 32 moves between the two positions shown in FIGS. 1 and 3. Bore 35 may also be of similar, close-fitting, non-circular cross section, specifically a teardrop-shape of similar size and shape to the outer surface of hypotube 14, so that hub 32 is non-rotatable relative to hypotube 14. This avoids accidental rotation, which can damage stent 28.

Typically, sheath 30 is of circular cross section, as is catheter body 12.

Thus, a catheter is provided which can be advanced into a patient without the need for a guiding catheter. Then, the stent or other medical device of implantation can be located by means of flow of x-ray contrast media passing out of the distal end portion of the catheter, without removal of the guidewire along which the catheter may be advanced, with improved contrast media flow rates. The sheath that surrounds the implantable medical device such as a stent can be retracted when the device is properly positioned, and the device may be emplaced with great reliability and ease.

The above has been offered for illustrative purposes only, and is not intended to limit the scope of the invention of this application, which is as defined in the claims below.

That which is claimed:

1. The method of deploying an implantable medical stent within a patient, which comprises:

advancing a catheter having a balloon into said patient, said catheter carrying said stent in a position surrounding said catheter balloon, said catheter and sheath defining proximal ends and being connected together at said ends each to a separate hub, said catheter also carrying an outer, semi-flexible sheath surrounding at least part of said catheter and said stent, the stent and semi-flexible sheath being advanced together into the patient with said catheter to position the stent at a desired location while enclosed in said sheath, said catheter defining a proximal portion of non-circular cross section;

retracting said sheath to expose said stent to the exterior, one of said hubs and said sheath slidingly moving along the proximal portion during said retracting step from an advanced position surrounding said stent to a retracted position where the sheath is longitudinally spaced from said stent, the hub connected to said sheath, sliding in said step of retracting said sheath between said advanced and retracted positions, being prevented from rotation about the longitudinal axis of said catheter by said proximal portion of non-circular cross section;

inflating said balloon to radially expand said stent; and withdrawing said catheter and sheath from the patient.

2. The method of claim 1 in which said catheter, stent, and sheath are advanced into the patient without the use of a guiding catheter.

3. The method of claim 1 in which said sheath defines side holes positioned adjacent to said stent to facilitate the flow of x-ray contrast fluid out of said sheath.

4. The method of claim 1 in which said sheath has a wall thickness of no more than about 0.015 inch, and is of sufficient stiffness to avoid wrinkling and axial collapsing as the sheath is advanced with said catheter and stent into the patient.

5. The method of claim 4 in which said sheath is made of polyimide plastic.

6. The method of claim 1 in which said hub connected to the sheath has a lock to secure said sheath and hub in the advanced position.

7. The method of claim 1 comprising the further step of passing x-ray contrast fluid to the vicinity of said stent between said catheter and said sheath, and x-ray visualizing the position of said stent.

8. The method of claim 1 in which said sheath defines a distal end, and said catheter defines a distal tip, said sheath distal end being releasably retained by said distal tip until said sheath is retracted.

9. The method of deploying a stent within a patient, which comprises:

advancing a catheter having a guidewire lumen and a balloon into said patient, said catheter carrying said stent in a position surrounding said catheter balloon, said catheter also carrying an outer, semi-flexible sheath surrounding at least part of said catheter and said stent, the stent and semi-flexible sheath being advanced together into the patient with said catheter to position the stent at a desired location while enclosed in said sheath;

retracting said sheath to expose said stent to the exterior;

inflating said balloon to radially expand said stent;

withdrawing said catheter and sheath from the patient;

and further comprising the step of passing x-ray contrast fluid to the vicinity of said stent between the catheter and said sheath and x-ray visualizing the position of said stent, whereby x-ray visualization can take place while a guidewire occupies said guidewire lumen.

10. The method of claim 9 in which said x-ray contrast fluid is passed to the vicinity of said stent prior to retracting said sheath to expose said stent to the exterior.

11. The method of claim 10 in which said catheter, stent, and sheath are advanced into the patient without the use of a guiding catheter.

12. The method of claim 11 in which said sheath has a wall thickness of no more than about 0.015 inch, and is of sufficient stiffness to avoid wrinkling and axial collapsing as the sheath is advanced with said catheter and stent into the patient.

13. The method of claim 12 in which said catheter and sheath define proximal ends and are connected together at said ends each to a hub, one of said hubs being slidably moved along said catheter during the step of retracting said sheath.

14. The method of claim 13 in which said catheter defines a proximal portion of non-circular cross section, the hub connected to said sheath sliding, in the step of retracting said sheath, on said proximal portion in a manner preventing rotation about the longitudinal axis of said catheter.

15. The method of claim 9 in which said sheath defines side holes positioned adjacent to said stent to facilitate the flow of x-ray contrast fluid out of said sheath.

16. A catheter for deploying an implantable medical device within a patient, which catheter comprises:

a tubular catheter body having a proximal and distal ends, said catheter carrying a inflatable balloon adjacent the distal end of said catheter, said catheter also carrying an outer, semi-flexible sheath surrounding said catheter balloon in a first position, said sheath being retractable from a position adjacent said proximal end to permit said sheath to be slidingly retracted to expose said balloon the exterior, said catheter comprising a flow system for providing x-ray contrast fluid in a tubular path between said catheter said outer, semi-flexible sheath, said catheter also defining a guidewire lumen, whereby x-ray visualization can take place while a guidewire occupies said guidewire lumen.

17. The catheter of claim 16 in which a stent is carried on said catheter in a position surrounding said balloon, whereby expansion of said balloon causes expansion of said stent.

18. The catheter of claim 16 in which said sheath defines a distal end portion having side holes to facilitate the flow of x-ray contrast fluid out of said sheath in the vicinity of said catheter balloon.

19. The catheter of claim 18 in which said sheath has a wall thickness of no more than about 0.015 inch, and is of sufficient stiffness to avoid wrinkling and axial collapsing as said sheath is advanced with said catheter into a patient.

20. The catheter of claim 19 in which said sheath is made of polyimide plastic.

21. The catheter of claim 16 in which said catheter body and sheath each define proximal ends which are connected each to a separate hub, one of said hubs and said sheath being slidably movable along said catheter body between an advanced position in which a distal end of said sheath surrounds said catheter balloon and a retracted position where the sheath is longitudinally spaced from said catheter balloon.

22. The catheter of claim 21 in which said catheter body defines a proximal portion of non-circular cross section, said hub connected to said sheath being slidable between said advanced and retracted positions in a manner preventing rotation about the longitudinal axis of said catheter.

23. The catheter of claim 22 in which said hub connected to said sheath has a lock to hold said sheath and hub in the advanced position.

24. The catheter of claim 16 in which said sheath defines a distal end and said catheter defines a distal tip, said sheath distal end being releasably retained by the distal tip when the sheath is in the advanced position.

25. A catheter for deploying an implantable medical device within a patient, which catheter comprises:

a tubular catheter body having proximal and distal ends, said catheter carrying an inflatable balloon adjacent said distal end of said catheter, said catheter also carrying an outer, semi-flexible sheath surrounding said catheter balloon in a first position, said sheath being slidingly retractable from a position adjacent said proximal end to expose said balloon to the exterior, said catheter body and sheath each defining proximal ends which are connected each to a separate hub, one of said hubs and said sheath being slidingly movable along said catheter body between said first position and a retracted position where the sheath is longitudinally spaced from the catheter balloon, and in which said catheter body defines a proximal portion of non-circular cross section, said hub connected to said sheath being slidable along said proximal portion between said first and retracted positions in a manner preventing rotation about the longitudinal axis of said catheter.

26. The catheter of claim 25 in which said hub connected to said sheath has a lock to hold said sheath and hub in the advanced position.

27. The catheter of claim 25 in which said sheath has a wall thickness of no more that about 0.015 inch, and is of sufficient stiffness to avoid wrinkling and axial collapsing as said sheath is advanced with said catheter into a patient.

28. The catheter of claim 25 in which said catheter body defines a distal tip, and said sheath defines a distal end, the sheath distal end being releasably retained by the distal tip when the sheath is in the first, advanced position.

29. The catheter of claim 28 in which said sheath defines a distal end portion having side holes to facilitate the flow of x-ray contrast fluid out of said sheath into the vicinity of said catheter balloon.

* * * * *